United States Patent
Proksa

(10) Patent No.: US 10,610,183 B2
(45) Date of Patent: Apr. 7, 2020

(54) SYSTEM AND METHOD FOR ASSISTING IN ASSESSING A STATE OF A SUBJECT'S LUNGS

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/070,897

(22) PCT Filed: Dec. 21, 2017

(86) PCT No.: PCT/EP2017/083965
§ 371 (c)(1),
(2) Date: Jul. 18, 2018

(87) PCT Pub. No.: WO2018/115215
PCT Pub. Date: Jun. 28, 2018

(65) Prior Publication Data
US 2019/0298292 A1    Oct. 3, 2019

(30) Foreign Application Priority Data
Dec. 23, 2016    (EP) .................................... 16206673

(51) Int. Cl.
*G06K 9/00*    (2006.01)
*A61B 6/00*    (2006.01)
(Continued)

(52) U.S. Cl.
CPC ............ *A61B 6/5205* (2013.01); *A61B 5/004* (2013.01); *A61B 5/08* (2013.01); *A61B 6/032* (2013.01);
(Continued)

(58) Field of Classification Search
None
See application file for complete search history.

(56) References Cited

U.S. PATENT DOCUMENTS 7,693,256 B2    4/2010  Brahme
9,076,201 B1 *  7/2015  Negahdar ............. G06T 7/0012
(Continued)

FOREIGN PATENT DOCUMENTS

| CN | 205019076 | 2/2016 |
|---|---|---|
| WO | WO2006137294 A1 | 12/2006 |
| WO | 2016/058838 | 4/2016 |

OTHER PUBLICATIONS

Yaroshenko, et al., "Grating-based X-ray dark-field imaging: a new paradigm in radiology", Current Radiology Reports, vol. 2, No. 2, May 23, 2014.

(Continued)

*Primary Examiner* — Atiba O Fitzpatrick
(74) *Attorney, Agent, or Firm* — Larry Liberchuk

(57) ABSTRACT

The invention relates to a system (1) for assisting in assessing a state of a subject's lung. The system is adapted to process a dark field image, which comprises dark field values for different spatial positions and for different breathing state values, such that a differentiation image is generated by differentiating the provided dark field image with respect to the breathing state values. This differentiation can lead to a functional image which can be used for detecting changes of air-soft tissue interfaces, which might be caused by a lung disease, with high sensitivity. This allows for an improved assisting in assessing a state of a subject's lung.

10 Claims, 2 Drawing Sheets

(51) Int. Cl.
*A61B 6/03* (2006.01)
*G06T 5/00* (2006.01)
*G06T 7/00* (2017.01)
*A61B 5/08* (2006.01)
*A61B 5/00* (2006.01)

(52) U.S. Cl.
CPC .............. *A61B 6/484* (2013.01); *A61B 6/50* (2013.01); *G06T 5/003* (2013.01); *G06T 7/0012* (2013.01); *A61B 6/4035* (2013.01); *A61B 6/4291* (2013.01); *G06T 2207/20201* (2013.01); *G06T 2207/30061* (2013.01)

(56) References Cited

U.S. PATENT DOCUMENTS

| 9,990,735 | B2 | 6/2018 | Toyama |
| 2014/0212014 | A1* | 7/2014 | Kim ...................... G06T 3/0068 382/131 |

OTHER PUBLICATIONS

Meinel, et al., "Diagnosing and Mapping Pulmonary Emphysema on X-Ray Projection Images: Incremental Value of Grating-Based X-Ray Dark-Field Imaging", PLOS ONE, vol. 8, No. 3, Mar. 26, 2013.

Christensen, et al., "Tracking lung tissue motion and expansion/compression with inverse consistent image registration and spirometry", Medical Physics, vol. 34, No. 6, May 21, 2007.

Kitchen, et al., "Dynamic measures of regional lung air volume using phase contrast x-ray imaging", Phys. Med. Biol. 53 (2008) 6065-6077.

Hooper, et al., "Imaging Lung Aeration and Lung Liquid Clearance at Birth using Phase Contrast X-ray Imaging"; Clinical and Experimental Pharmacology and Physiology (2009) 36, 117-125.

Velroyen, et al., "Grating-based X-ray Dark-field Computed Tomography of Living Mice"; EBioMedicine 2 (2015) 1500-1506.

Yaroshenko, et al., "Pulmonary Emphysema Diagnosis with a reclinical Small-Animal X-ray Dark-Field Scatter-Contrast Scanner"; Radiology: vol. 269: No. 2—Nov. 2013.

Yaroshenko, et al,. "Small-Animal Dark-Field Radiography for Pulmonary Emphysema Evaluation"; Medical Imaging 2014.

Schleede, et al., "Emphysema diagnosis using X-ray dark-field imaging at a laser-driven compact synchrotron light source"; PNAS, Oct. 30, 2012, vol. 109, No. 44.

* cited by examiner

SYSTEM AND METHOD FOR ASSISTING IN ASSESSING A STATE OF A SUBJECT'S LUNGS

CROSS REFERENCE TO RELATED APPLICATIONS

This application is the U.S. National Phase application under 35 U.S.C. § 371 of International Application No. PCT/EP2017/083965, filed Dec. 21, 2017, published as WO 2018/115215 on Jun. 28, 2018, which claims the benefit of European Patent Application Number 16206673.2 filed Dec. 23, 2016. These applications are hereby incorporated by reference herein.

FIELD OF THE INVENTION

The invention relates to a system, method and computer program for assisting in assessing a state of a subject's lung.

BACKGROUND OF THE INVENTION

A system for assisting in assessing a state of a subject's lung is, for instance, an absorption computed tomography imaging system. An absorption computed tomography imaging system comprises an x-ray source and an x-ray detector, which are rotatable around a subject's lung to be imaged such that x-rays generated by the x-ray source traverse the lung in different directions. The x-ray detector detects the x-rays after having traversed the lung and generates projection data based on the detected x-rays, wherein a reconstruction unit reconstructs an absorption computed tomography image based on the generated projection data.

In the absorption computed tomography image air-soft tissue interfaces are not very well detectable, thereby reducing the usability of the absorption computed tomography image for assisting in assessing a state of a subject's lung.

SUMMARY OF THE INVENTION

It is an object of the present invention to provide a system, method and computer program which allow for an improved assisting in assessing a state of a subject's lung.

In a first aspect of the present invention a system for assisting in assessing a state of a subject's lung is presented, wherein the system comprises:
- a dark field image providing unit for providing a dark field image of the lung, wherein the provided dark field image comprises dark field values for different spatial positions and for different breathing state values being indicative of a breathing state of the lung,
- an image processing unit for processing the provided dark field image, wherein the image processing unit is adapted to determine a differentiation image by differentiating the provided dark field image with respect to the breathing state values.

In the dark field image air-soft tissue interfaces of the lung, particularly of the alveoli, are very well detectable. By differentiating this dark field image with respect to the breathing state values a functional image can be provided, which can be used for detecting changes of air-soft tissue interfaces, which might be caused by a lung disease, with high sensitivity. This allows for an improved assisting in assessing a state of a subject's lung.

The dark field image providing unit can be a storing unit, in which the dark field image is stored, in order to allow the dark field image providing unit to provide the dark field image. The dark field image providing unit can also be a receiving unit for receiving the dark field image from an imaging system being adapted to generate the dark field image. The dark field image providing unit can also be the imaging system itself. The imaging system can be adapted to generate as the dark field image a projection image and/or a computed tomography image.

In an embodiment the dark field image providing unit is adapted to provide the dark field image such that the dark field values are provided for different breathing state values being dependent on a difference between a current lung volume and a reference lung volume. For instance, the reference lung volume can be the lung volume for maximal inhale or maximal exhale. It is also possible that the dark field image providing unit is adapted to provide the dark field image such that the dark field values are provided for different breathing state values being dependent on an absolute lung volume. Moreover, the dark field image providing unit can be adapted to provide the dark field image such that the dark field values are provided for different breathing state values being dependent on a time within a breathing cycle. If the dark field image is differentiated with respect to these kinds of breathing state values, the usability of the differentiation image for detecting changes in air-soft tissue interfaces and hence for assisting in assessing a state of a subject's lung can be further improved.

The image processing unit can be adapted to integrate absolute image values of the differentiation image over the breathing state values and/or over the spatial positions. This integration can be performed, for instance, over the entire breathing state values or the entire spatial positions, respectively, or over a spatial region of interest or over an interesting region of breathing state values, respectively. The integration over the breathing state values yields an integration image. The integration result allows for a further improved assisting in assessing a state of a subject's lung. It should be noted that the expression "A and/or B" preferentially includes following options a) A without B, b) B without A, and c) A and B.

It is preferred that the image processing unit is further adapted to apply a motion correction algorithm to the provided dark field image before determining the differentiation image, wherein the motion correction algorithm is preferentially an elastic motion correction algorithm. By correcting motion artifacts in the provided dark field image before determining the differentiation image, the quality of the differentiation image can be further improved, thereby allowing for a further improved assistance in assessing a state of a subject's lung.

In another aspect of the present invention a method for assisting in assessing a state of a subject's lung is presented, wherein the method comprises:
- providing a dark field image of the lung by a dark field image providing unit, wherein the provided dark field image comprises dark field values for different spatial positions and for different breathing state values being indicative of a breathing state of the lung,
- processing the provided dark field image by an image processing unit, wherein the image processing unit is adapted to determine a differentiation image by differentiating the provided dark field image with respect to the breathing state values.

In a further aspect of the present invention a computer program for assisting in assessing a state of a subject's lung is presented, wherein the computer program comprises program code means for causing a system as defined in claim 1 to carry out the method as defined in claim 9, when the computer program is run on the system.

It shall be understood that the system of claim 1, the method of claim 9 and the computer program of claim 10, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
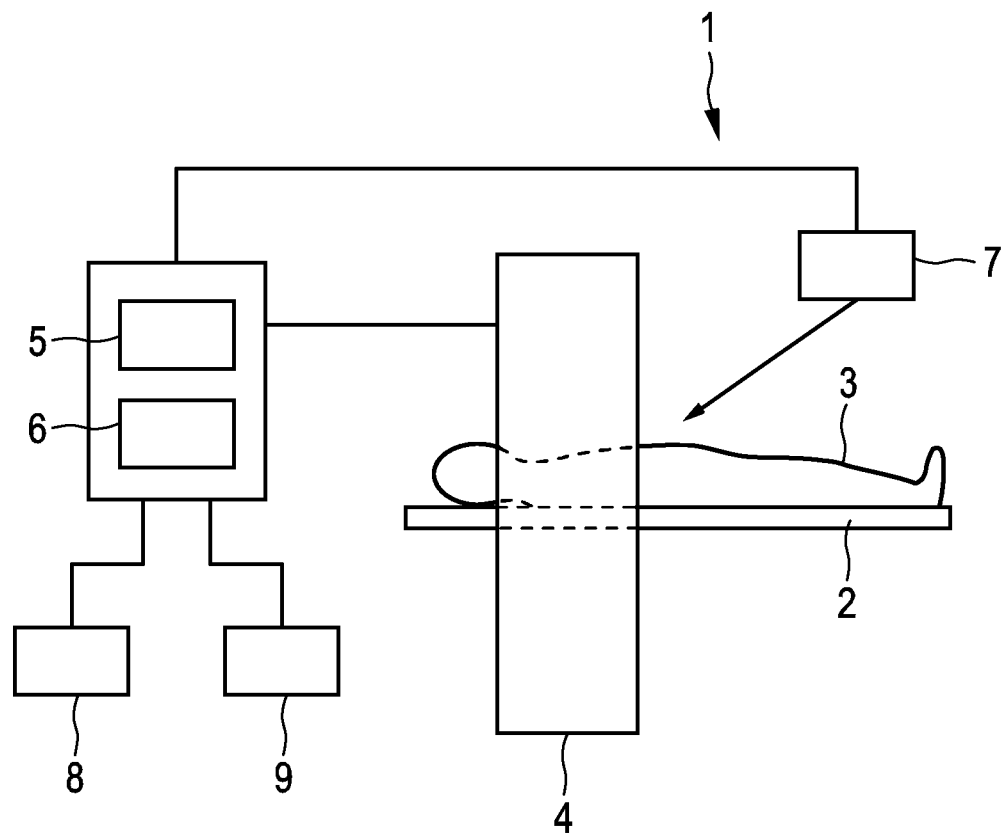
FIG. 1 shows schematically and exemplarily an embodiment of a system for assisting in assessing a state of a subject's lung.

FIG. 1 shows schematically and exemplarily an embodiment of a system for assisting in assessing a state of a subject's lung. The system 1 comprises an acquisition device 4 for acquiring dark field projection data in different acquisition directions. For acquiring the dark field projection data well known techniques can be used, which employ a grating based x-ray phase contrast interferometer, like the techniques disclosed in the article "Grating-based X-ray dark-field imaging: a new paradigm in radiography" by A. Yaroshenko et al., Current Radiology Reports, 2:57 (2014), which is herewith incorporated by reference.

The system 1 further comprises a breathing state determination unit 7 for determining the breathing state of a subject 3 lying on a support means 2 like a patient table. The acquisition device 4 is adapted to acquire dark field projection data of the lung of the subject 3, wherein simultaneously breathing state values being indicative of the respective breathing state of the subject 3 are determined by the breathing state determination unit 7 such that the acquired dark field projection data can be assigned to the breathing states, i.e. to the breathing state values. The breathing state determination unit 7 can use a chest belt or another means for determining the respective breathing state. The breathing state values can be, for instance, times within a breathing cycle, they can be values being indicative of the absolute lung volume, or they can be dependent on a difference between a current lung volume and a reference lung volume which might be the lung volume for maximal inhale or maximal exhale.

The system 1 further comprises a reconstruction unit 5 for reconstructing a dark field computed tomography image of the lung based on the acquired dark field projection data and the breathing state values such that for different breathing states a respective dark field computed tomography image of the lung is reconstructed. The reconstructed dark field image of the lung can be regarded as being an image having two or three spatial dimensions and a further dimension indicating the respective breathing state. Since the acquisition device 4, the breathing state determination unit 7 and the reconstruction unit 5 are adapted to generate and hence provide the dark field image of the lung, these components can be regarded as being components of a dark field image providing unit.

The system 1 further comprises an image processing unit 6 being adapted to apply a motion correction algorithm to the provided dark field image, wherein in this embodiment the motion correction algorithm is an elastic motion correction algorithm. In particular, the dark field values for different breathing state values, i.e. corresponding spatial images for respective breathing states, can be elastically registered to each other, in order to determine a registration transformation being indicative of the motion of the lung tissue. This registration transformation, i.e. the determined motion, can then be used for correcting motion artifacts in the provided dark field image. Optionally, additional motion information being indicative of the motion of the lung obtained from a sensor like a spirometer is also used for correcting the motion artifacts. For instance, the motion correction technique disclosed in the article "Tracking lung tissue motion and expansion/compression with inverse consistent image registration and spirometry" by G. Christensena, Medical Physics, volume 34, number 6 (2007) can be used, which is herewith incorporated by reference.

The image processing unit 6 is further adapted to determine a differentiation image by differentiating the provided dark field image with respect to the breathing state values. This differentiation can be described by following equation:

$$L(\vec{x}, b) = \frac{\partial g(\vec{x}, b)}{\partial b}, \quad (1)$$

wherein $g(\vec{x}, b)$ denotes dark field values of the dark field image for different spatial positions $\vec{x}$ and for different breathing state values b and wherein $L(\vec{x}, b)$ denotes image values of the differentiation image for the different spatial positions $\vec{x}$ and the different breathing state values b.

The system 1 further comprises an input unit 8 for allowing a user to provide inputs into the system 1 like commands for starting or stopping a procedure for generating dark field images, determining differentiation images, et cetera. Moreover, the system 1 comprises a display unit 9 for displaying the differentiation image and the provided dark field image. In particular, the display unit 9 can show a spatial distribution $L(\vec{x}, b_{ref})$ of the lung structure change for a reference state $b_{ref}$, i.e. it can show a map illustrating a spatial lung structure change distribution for the reference state $b_{ref}$ which can be useful for differentiating active and inactive lung areas. Moreover, the display unit 9 can show the function $L(\vec{x}_{ref}, b)$ for a reference spatial position $\vec{x}_{ref}$, which illustrates the temporal lung structure change at the reference position $\vec{x}_{ref}$. The reference position $\vec{x}_{ref}$ and the reference breathing state value $b_{ref}$ may be selectable by a user via the input unit 8.

The dark field projection data and the reconstructed dark field computed tomography image provide information about the microstructure of tissue below the spatial resolution of known attenuation projection data and known absorption computed tomography images. This provides valuable information in lung imaging where the air-soft tissue interfaces of the alveoli generate a strong dark field signature. Changes of this structure relative to healthy tissue caused, for instance, by lung diseases can be detected with high sensitivity. In particular, chronic obstructive pulmonary disease (COPD), pneumonia and/or lung fibrosis can be detected.

The breathing state of the lung influences the microstructure of the lung, thereby causing a dependency of the dark field signal on the breathing state. The system 1 described above with reference to FIG. 1 makes use of this dark field dependency on the breathing state, in order to obtain functional lung information, wherein based on the dark field values $g(\vec{x},b)$, which could also be regarded as being local dark field values, the functional lung tissue parameter $L(\vec{x},b)$ is determined, wherein this parameter $L(\vec{x},b)$ could also be regarded as being a quantity defining the differential lung structure change. The local value $L(\vec{x},b)$ indicates micro structural changes in the lung while breathing.

The image processing unit 6 can be adapted to generate an integration image by integrating absolute image values of the differentiation image over the breathing state values. Thus, for instance, an integration image $I(\vec{x})$ may be generated in accordance with following equation:

$$I(\vec{x}) = \int \|L(\vec{x},b)\| db. \quad (2)$$

In this image lung areas that do not actively contribute to breathing may show small values compared to other lung areas such that the integration image $I(\vec{x})$ is very well usable for assisting in assessing the state of the lung. It is also possible to generate a breathing state dependent integration value $I(b)$ by integrating over the spatial positions in accordance with following equation:

$$I(b) = \int \|L(\vec{x},b)\| d\vec{x}. \quad (3)$$

This integration can be performed over all spatial positions or only over a spatial region of interest. In the latter case the result can indicate micro structural changes in the region of interest while breathing.

The dark field image providing unit 4, 5, 7 can be adapted to determine the dark field image $g(\vec{x},b)$ for a set of b's and to numerically determine the differentiation image from this discrete set in accordance with following equation:

$$L(\vec{x}, b) \approx \frac{\Delta g(\vec{x}, b)}{\Delta b}, \quad (4)$$

wherein $\Delta g(\vec{x},b)$ denotes the difference between a) the dark field value at the spatial position $\vec{x}$ for the breathing state value b and b) the dark field value at the spatial position $\vec{x}$ for an adjacent breathing state. Correspondingly, $\Delta b$ denotes a difference between the breathing state b and the adjacent breathing state. Since the lung tissue will be deformed during the breathing, a motion correction is preferentially applied before this calculation as described above.

The breathing state value may be defined in accordance with following equation:

$$b = \frac{V - V_{ex}}{V_{in} - V_{ex}}, \quad (5)$$

wherein V denotes a value being indicative of the current volume of the lung, $V_{ex}$ denotes a value being indicative of the volume of the lung for maximal exhale and wherein $V_{in}$ denotes a value being indicative of the volume of the lung for maximal inhale. The variable b can also be defined in another way for indicating, for instance, the absolute lung volume or the time within a breathing cycle.

Figure 2:
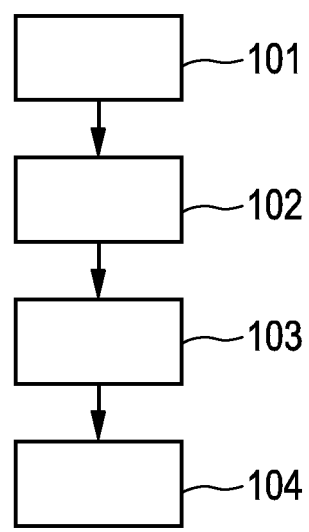
FIG. 2 shows a flowchart exemplarily illustrating a method for assisting in assessing a state of a subject's lung.

FIG. 2 shows a flowchart exemplarily illustrating an embodiment of a method for assisting in assessing a state of a subject's lung.

In step 101 a dark field image of the lung is provided by the dark field image providing unit 4, 5, 7, wherein the provided dark field image comprises dark field values for different spatial positions and for different breathing state values being indicative of a breathing state of the lung. In step 102 a motion correction algorithm is applied to the provided dark field image. In particular, an elastic motion correction algorithm is applied to the provided dark field image. In step 103 a differentiation image is determined by differentiating the provided dark field image with respect to the breathing state values by the image processing unit 6. In step 104 the differentiation image is shown on the display unit 9.

Although in above described embodiments the provided dark field image is a computed tomography image, the provided dark field image can also be a projection image, wherein in this case the dark field projection image is differentiated with respect to the breathing state value for determining the differential lung structure change $L(\vec{x},b)$. Moreover, although in above described embodiments the dark field computed tomography image has been reconstructed based on dark field projection images, the dark field computed tomography image can also be directly reconstructed from raw data obtained from the x-ray based phase contrast interferometer, i.e. without generating intermediate dark field projection images. For more details of corresponding known dark field techniques reference is made to the above mentioned article by A. Yaroshenko et al.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the reconstruction of a computed tomography image, the determination of a differentiation image, the motion correction, et cetera performed by one or several units or devices can be performed by any other number of units or devices. These operations and/or the control of the system for assisting in assessing a state of a subject's lung in accordance with the method for assisting in assessing a state of a subject's lung can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for assisting in assessing a state of a subject's lung. The system is adapted to process a dark field image, which comprises dark field values for different spatial positions and for different breathing state values, such that a differentiation image is generated by differentiating the provided dark field image with respect to the breathing state values. This differentiation can lead to a functional image which can be used for detecting changes of air-soft tissue interfaces, which might be caused by a lung disease, with high sensitivity. This allows for an improved assisting in assessing a state of a subject's lung.

The invention claimed is:

1. A system for assisting in assessing a state of a subject's lung, the system comprising:
   a dark field image providing unit for providing a dark field image of the lung, wherein the provided dark field image comprises dark field values for different spatial positions and for different breathing state values being indicative of a breathing state of the lung,
   an image processing unit for processing the provided dark field image, wherein the image processing unit is adapted to determine a differentiation image by differentiating the provided dark field image with respect to the breathing state values.

2. The system as defined in claim 1, wherein the dark field image providing unit is adapted to provide the dark field image such that the dark field values are provided for different breathing state values being dependent on a difference between a current lung volume and a reference lung volume.

3. The system as defined in claim 2, wherein the reference lung volume is the lung volume for maximal inhale or maximal exhale.

4. The system as defined in claim 1, wherein the dark field image providing unit is adapted to provide the dark field image such that the dark field values are provided for different breathing state values being dependent on an absolute lung volume.

5. The system as defined in claim 1, wherein the dark field image providing unit is adapted to provide the dark field image such that the dark field values are provided for different breathing state values being dependent on a time within a breathing cycle.

6. The system as defined in claim 1, wherein the image processing unit is further adapted to integrate absolute image values of the differentiation image over the breathing state values and/or over the spatial positions.

7. The system as defined in claim 1, wherein the image processing unit is further adapted to apply a motion correction algorithm to the provided dark field image before determining the differentiation image.

8. The system as defined in claim 7, wherein the motion correction algorithm is an elastic motion correction algorithm.

9. A method for assisting in assessing a state of a subject's lung, the method comprising:
   providing a dark field image of the lung by a dark field image providing unit, wherein the provided dark field image comprises dark field values for different spatial positions and for different breathing state values being indicative of a breathing state of the lung,
   processing the provided dark field image by an image processing unit, wherein the image processing unit is adapted to determine a differentiation image by differentiating the provided dark field image with respect to the breathing state values.

10. A non-transitory computer-readable medium having one or more executable instructions stored thereon which, when executed by at least one processor, cause the at least one processor to perform a method for assisting in assessing a state of a subject's lung, the method comprising:
    providing a dark field image of the lung by a dark field image providing unit, wherein the provided dark field image comprises dark field values for different spatial positions and for different breathing state values being indicative of a breathing state of the lung; and
    processing the provided dark field image by an image processing unit, wherein the image processing unit is adapted to determine a differentiation image by differentiating the provided dark field image with respect to the breathing state values.

* * * * *